United States Patent
Kane et al.

(10) Patent No.: US 10,300,092 B2
(45) Date of Patent: May 28, 2019

(54) BEE BLOOM COMPOSITIONS, METHODS OF EXTRACTION AND USES THEREOF

(75) Inventors: Penny Colleen Kane, Calgary (CA); Ronald Duncan Mathison, Calgary (CA)

(73) Assignee: KANE, Penny Coleen, Calgary (CA)

(*) Notice: Subject to any disclaimer, the term of this patent is extended or adjusted under 35 U.S.C. 154(b) by 55 days.

(21) Appl. No.: 13/978,703

(22) PCT Filed: Jan. 6, 2012

(86) PCT No.: PCT/CA2012/000020
§ 371 (c)(1),
(2), (4) Date: Oct. 22, 2013

(87) PCT Pub. No.: WO2012/092673
PCT Pub. Date: Jul. 12, 2012

(65) Prior Publication Data
US 2014/0037751 A1 Feb. 6, 2014

Related U.S. Application Data

(60) Provisional application No. 61/430,965, filed on Jan. 8, 2011.

(51) Int. Cl.
| | |
|---|---|
| A61K 35/644 | (2015.01) |
| A23L 21/20 | (2016.01) |
| A23L 33/115 | (2016.01) |
| A23L 33/175 | (2016.01) |
| A23L 33/18 | (2016.01) |

(52) U.S. Cl.
CPC ............ *A61K 35/644* (2013.01); *A23L 21/20* (2016.08); *A23L 33/115* (2016.08); *A23L 33/175* (2016.08); *A23L 33/18* (2016.08)

(58) Field of Classification Search
CPC .................. A61K 2300/00; A61K 35/644
See application file for complete search history.

(56) References Cited

U.S. PATENT DOCUMENTS

| | | | |
|---|---|---|---|
| 2,494,907 A | 1/1950 | Small | |
| 4,623,667 A * | 11/1986 | Gans et al. | 514/762 |
| 6,342,255 B1 | 1/2002 | De Gregorio | |
| 6,482,442 B1 | 11/2002 | Dado | |
| 6,579,543 B1 | 6/2003 | McClung | |
| 6,649,178 B2 | 11/2003 | Mohammadi et al. | |
| 7,141,611 B2 | 11/2006 | Gamble et al. | |
| 7,351,739 B2 | 4/2008 | Ho et al. | |
| 7,763,282 B2 | 7/2010 | Corvi Mora et al. | |
| 2005/0048128 A1 | 3/2005 | Miyata et al. | |
| 2010/0034905 A1 | 2/2010 | Sembrano | |
| 2010/0074964 A1 | 3/2010 | Glavas | |

FOREIGN PATENT DOCUMENTS

CA 1233416 3/1988

OTHER PUBLICATIONS

Ciapaite et al. (2007) Biochimica et Biophysica Acta 1771: pp. 147-154.*
Coll et al. (2008) JBC, 283: 11107-11116.*
Kennedy et al. (2009) J. Nutr. 139: 1-4.*
Kurstjens et al. (1990) Naturwissenshaften 77, pp. 34-35.*
Miele et al. (1988) Nature vol. 335, pp. 726-730.*
Tomas-Barberan et al. (1993) Z. Naturforsch. 48c, pp. 68-72.*
Zhao et al. (2005) Biochem. and Biophys. Res. Comm. 336, pp. 909-917.*
Revilla et al. (1998) J. Agric. Food Chem. 46: pp. 4592-4597.*
Raskin et al. (2004) Current Pharmaceutical Design, 10, pp. 3419-3429.*
Blomquist et al. (1985) Comp. Biochem. Physiol. vol. 82B, No. 1, pp. 137-142.*
Buchwald et al. (2008) The Journal of Experimental Biology, 211, pp. 121-127.*
Saleem et al. (2009) Cancer Letters 285: 109-115.*
Website Document entitled "Beverly's Bees" (http://www.beverlybees.com/cutting-comb-is-a-sticky-gooey-mess). Posted Jul. 8, 2011. Downloaded from website Jun. 18, 2014.*
Garcia-Viguera et al. (1992) Z. Naturforsch. 47c, 634-637.*
Tulloch (1969) Lipids col. 5, No. 2, 247-258.*
El-Demerdash (2011) Toxicology and Applied Pharmacology 254: 238-244.*
Carbajal, D., et al. "Anti-inflammatory activity of D-002: an active product isolated from beeswax." Prostaglandins, Leukotrienes and Essential Fatty Acids, vol. 59, No. 4, Oct. 1998, pp. 235-238.
Canadian Intellectual Property Office, International Search Report of PCT/CA2012/000020, dated May 3, 2012, WIPO, 3 pages.
Li Guang, Modern Study on Bees, China Medical Herald, Feb. 28, 2010, 7(6), pp. 11-13, China.
Gong Mi, Covering on the Surface of Beeswax-Bloom, Journal of Bee, Apr. 30, 1992, No. 4, pp. 26-27, China.
Abu Ali Ibn-e-Sina Al-Qaanoon-fil-Tibb, vol. II 05 (p. 04-08) ( Ref.p. of publication:392 ) 1987 AD Institute of History of Medicine and Medical Research, Jamia Hamdard New Delhi-62, India.†
Mohammad Najmul Ghani Khan Khazaain-al-Advia, vol. I 05 (p. 09-13) ( Ref.p. of publication:686 ). 1911 AD Nadeem Yunus Printer / Sheikh Mohd Basheer & Sons Lahore.†
Rasatantrasarah Evam Siddhaprayogasamgrahah;—part II 05 (p. 14-18) ( Ref.p. of publication:328-329 ) Edn 8th; 1990 Krishan Gopal Ayurveda Bhawan. India.†

* cited by examiner
† cited by third party

*Primary Examiner* — Christopher R Tate
*Assistant Examiner* — Russell G Fiebig
(74) *Attorney, Agent, or Firm* — Bennett Jones LLP (57) ABSTRACT

The present invention relates to purified compositions of bee bloom, methods of preparing the purified compositions of bee bloom and the use of bee bloom in the reducing and treatment of inflammation.

7 Claims, 1 Drawing Sheet

BEE BLOOM COMPOSITIONS, METHODS OF EXTRACTION AND USES THEREOF

FIELD OF THE INVENTION

The present invention relates to the field of natural products for the treatment of inflammation, extracted and purified from wax bloom.

BACKGROUND OF THE INVENTION

Inflammation affects many individuals and is an underlying condition in a variety of diseases generally, inflammation is a body's defensive response to harmful stimuli used by animals to protect damaged areas and assist healing processes. As is known, pathogens, irritants, or damaged cells can trigger the inflammatory response leading to both acute and chronic forms of inflammation. Acute inflammation is generally defined as the body's initial response to harmful stimuli which involves increasing the movement of plasma and leukocytes to the injured area. Chronic inflammation is generally defined as the body's prolonged response to damaged tissue that leads to increased blood flow to and swelling of tissues over longer periods of time.

Despite the contribution of inflammation to healing, a variety of conditions including allergic reactions, atherosclerosis and rheumatoid arthritis can result from the cascade of biochemical events involved in the inflammation process. For example, inflammation can result from exposure to allergens in which a sensitized immune system will initiate antibody production in response to foreign objects. In this case, inflammatory mediators, such as histamine, are released leading to itching, swelling and mucous production. In other examples, atherosclerosis results from chronic inflammation in the walls of arteries leading to plaque formation and arterial narrowing. Rheumatoid arthritis involves an inflammatory response that attacks the synovial joints of an individual leading to pain and disfigurement.

Five types of allergic reactions have been identified. These include: allergy (immediate, Type I), cytotoxic and antibody-dependent (Type II), immune complex mediated (Type III), delayed-type hypersensitivity, cell-mediated immune memory response and antibody-independent (Type IV), and autoimmune disease and receptor mediated (Type V) Immediate or Type I allergic reactions are largely attributed to IgE antibodies, although IgG antibodies can participate in and modulate allergic reactions The allergy is generally caused by the activation of a subpopulation of immune cells, the mast cells and basophils when antigen reacts with IgE antibody receptors on the cell's surface the chemical mediators initiate the allergic reaction by acting on adjacent immune, epithelial, endothelial and smooth muscle cells and promote, in a longer term, the influx of other inflammatory and immune cells (neutrophils, eosinophils, monocytes, lymphocytes) into tissue. This influx of inflammatory cells predisposes the patient to recurrent and sometimes delayed, or prolonged allergic or hypersensitivity reactions. A distinction between immediate and delayed allergic reactions and delayed, chronic immune injury can also be made. The Type 1 allergic reactions are defined according to the location where they occur. Asthmatic reactions occur in the lungs, rhinitis in the nose, conjunctivitis, iritis and uveitis in the eyes, urticaria (hives), atopic dermatitis and eczema in the outer skin dermis, angioedema occurs in dermis subcutaneous tissue, mucosa and submucosal tissues. Systemic allergic reactions in the circulation and in the gastrointestinal system and are often life threatening.

Anaphylactic shock, the most severe form of allergy, is a medical emergency. It is often severe and sometimes can provoke a fatal systemic reaction in a susceptible individual upon exposure to a specific antigen (as wasp venom or penicillin) after previous sensitization. Anaphylactic shock is characterized by respiratory symptoms, fainting, itching, urticaria, swelling of the throat or other mucous membranes and a sudden decline in blood pressure. Symptoms of anaphylactic shock include dizziness, loss of consciousness, labored breathing, swelling of the tongue, blueness of the skin, bronchospasm, low blood pressure, and death.

Asthma can be defined clinically as a condition of intermittent, reversible airways obstruction, and manifests itself as several clinical entities: allergic asthma, bronchial asthma, exercise induced asthma, chemical induced asthma, and static asthma. Asthma can be divided into two types. Extrinsic asthma is generally triggered by external agents such as allergens (dust mites, pollen, stings, drugs, or foods), and is commonly diagnosed in early life. Intrinsic asthma, which generally develops later in life, can be triggered by congested and inflamed tissues, infection, endogenous catecholamines (e.g. adrenaline), drugs (e.g. aspirin), stress or exertion. Inflammation can also be triggered by a number of stimuli including heat and chemical burns, exposure to toxins, damaged tissue due to environmental exposure (e.g. frostbite), infections including bacteria, viruses, and parasites, physical injury, immune reactions including allergic reactions and autoimmune conditions, exposure to radiation, as well as the presence of foreign bodies such as splinters or dirt.

Symptoms of inflammation include redness of the affected area, swollen and/or sore joints, stiffness of joints and in some cases even loss of joint function. Fever, chills and fatigue may also be side effects of an inflammatory response in the individual. In addition to these side effects, a number of diseases can result from chronic inflammation including asthma, hay fever, tendonitis, bursitis, arthritis, diabetes, heart disease, atherosclerosis, atopic dermatitis (eczema), contact dermatitis, psoriasis, irritable bowel syndrome, Crohn's disease, colitis, ileitis, gastritis, diverticulitis, ulcerative colitis hepatitis, nephritis, lupus erythematosus, Alzheimer's disease, Parkinson's disease and even cancer.

Treating inflammation typically involves the use of pharmaceuticals such as non-steroidal and steroidal anti-inflammatory drugs, Non-steroidal anti-inflammatory drugs (NSAIDs) can include over the counter medications such as aspirin, ibuprofen or naproxen. NSAIDs generally work by blocking the cyclooxygenase enzymes responsible for the production of prostaglandins; a group of lipid compounds that promote inflammation. Other pharmaceuticals include methotrexate, sulfasalazine, anti-TNF medications, cyclophosphamide and mycophenolate.

Steroidal treatments often involve the use of corticosteroids that act on the immune system to block the production of substances that trigger allergic and inflammatory reactions. Like NSAIDs, corticosteroids inhibit prostaglandin production thereby reducing the normal inflammatory response in the individual.

Immune-selective anti-inflammatory derivatives (NSAIDs) are another class of anti-inflammatory compounds. Generally, (NSAIDs) are a class of peptides that alter the activation of immune cells (leukocytes) responsible for the inflammatory response.

Natural approaches can also be used to treat inflammation. Herbs such as willow bark, meadowsweet, ginger, ginseng, and licorice, have been shown to exhibit anti-inflammatory properties. Omega-3 fatty acids have also been shown to induce an anti-inflammatory response in addition to vitamins Bi 2, C and E and the minerals copper and zinc.

Nutraceuticals such as probiotics, which are defined as healthy microorganisms living in the intestinal tract of mammals, and prebiotics, the non-digestible food ingredients that stimulate the growth of healthy bacteria, have also shown anti-inflammatory properties. Symbiotics, which combine prebiotics with probiotics, can be used for treating, alleviating and reducing the symptoms associated with inflammation.

The disadvantages of the above treatments are the adverse effects that may be associated with direct use and/or combinational risk Both gastrointestinal and renal effects, which can lead to hypertension, are the most common side effects of NSAIDs use. Cardiovascular risk is possible as well as the potential to adversely affect the fetus during pregnancy. Since prostaglandins protect the stomach and assist in blood clotting, NSAIDs can lead to stomach ulcers and promote bleeding.

Corticosteroids impede the function of white blood cells which keep the immune system functioning properly. Over time, use of corticosteroids can affect the function of the adrenal glands responsible for the natural production of corticosteroids. They can also increase the risk of high blood pressure and bone diseases such as osteoporosis. Upset stomach and vomiting are common in addition to sleep problems and indigestion. The lowering of an individual's resistance to infection is a risk and prolonged use can lead to organ failure.

The use of prebiotics, probiotics or their combination (symbiotics) run the risk of having their therapeutic effect altered when added to food products. Different preparation methods may impart different health effects. As such, their quality can be difficult to guarantee. They may also cause gas and/or bloating due to the activity of the microorganisms.

Although the use of vitamins and minerals is generally regarded as safe, excess usage can lead to adverse side effects. Vitamin C can cause nausea and diarrhea when recommended allowances are exceeded while vitamin E can lead to weakness and fatigue. Vitamin B12 may induce diarrhea and insomnia in certain individuals.

Another natural source of anti-inflammatory compounds is various bee products. More specifically, the use of some bee products is known to offer an anti-inflammatory response when used as a nutraceutical or applied topically. Such bee products include beeswax, propolis, royal jelly, honey, bee bread and bee pollen.

By way of background and as is known, beeswax is a compound used by bees to construct honeycombs, and is composed of free fatty acids (12-14%), free primary fatty alcohols (1%), linear wax monoesters and hydroxy-monoesters (35-45%), complex wax esters (15-27%>, and odd numbered straight chain hydrocarbons (12-16%) with predominant chain lengths of C27-C33. The incorporation of pollen and propolis give beeswax its distinct yellow colour. Propolis is a resinous mixture collected by bees from botanical sources and is used as a sealant for repairing the beehive, Royal jelly is the bee secretion used to feed the larvae destined to become queen bees, which as a food source is used to trigger the development of queen morphology Honey is a food source for bees made using the nectar from flowers. Bee bread is pollen packed into granules using honey and nectar and is used as a method to store pollen and bee pollen is the main energy source for the bees.

The above bee products are understood to have a variety of health benefits and their incorporation into both food products and nutraceuticals are widespread and in high demand. For example, various bee products have been used as complimentary medicines to treat a variety of disorders. In addition to treating inflammation, bee products have been used to allegedly provide protection against cold and flu viruses, to enhance energy and libido, reduce stress and depression, regulate hormones, suppress an unhealthy appetite, moderate body weight, rebuild bones and tissue, treat impotence and stomach ulcers, and as a dietary supplement to fight against cancer, high cholesterol and cardiac conditions.

Specifically, bee pollen is used as a general prophylactic and is believed to provide protection against cold and flu viruses, enhance energy, libido, stamina and mood, reduce stress and depression, regulate hormones, suppress cravings and an unhealthy appetite, moderate body weight, rebuild bones, tissue and muscle, treat anemia, asthma, allergic conditions, impotence, bleeding stomach ulcers, altitude sickness, and as a dietary supplement has been used for cancer, high cholesterol, cardiac conditions [1,2], and treatment of the prostate [3]. The German Federal Board of Health has recognized bee pollen as a medicine [2], Propolis, due to its antimicrobial and immunomodulatory properties, is used by natural health practitioners to relieve inflammations, viral diseases, ulcers, skin disorders, treating the common cold, wounds and burns, sore throats and dental plaque [1,3]. Royal jelly is proposed to have benefits in treating weak bones, endocrine system disorders, arthritis, asthma, impotence and infertility, Parkinson's disease, retarded growth, bacterial infections, and other disorders [1]. The use of royal jelly for health purposes is not widely reported [3]. Even honey, a common food source, is a natural energy booster, immune system builder and an aid in many common ailments, such as cuts and burns, and sooth sore throats. It is an emollient and contains anti-microbial properties [1].

Bee pollen, which is a mixture of flower pollen, honeybee digestive juices, and nectar, is a rich source of protein, carbohydrate, vitamins, and minerals. It contains a variety of secondary plant products such as flavenoids, carotenoids, and terpenes [4]. Concerning its use in allergies, bee pollen induces oral desensitization in patients suffering from pollen allergy [5], and several recent animal studies have shown that bee pollen inhibits allergic reactions. Specifically, a phenolic extract of bee pollen inhibited paw edema, IgE (immunoglobulin E) and IgG1 (immunoglobulin G1) ovalbumin-specific production, leukocyte migration to the lungs (bronchoalveolar lavage; (BAL)), and eosinophil peroxidise (EPO) activity in lungs of ovalbumin-sensitized mice. Daily oral administration of bee pollen to mice significantly reduced the IgE specific antigen elicited cutaneous mast cell activation, and in vitro reductions were seen in mast cell degranulated and tumor necrosis factor production consequent to inhibition of IgE binding to receptors (FcERI) could read Fc.di-elect cons.RI [6].

Higher aliphatic primary alcohols purified from beeswax (Apis mellifera) have cytoprotective effects and exhibit moderate anti-ulcer effects in animals and humans [7]. Triacontanol is the most abundant component this mixture, called D-002, followed by octacosanol and hexacosanol, while tetracosanol, dotriacontanol, and tetratriacontanol are present in lower concentrations [8]. Literature citations on beeswax and allergy generally indicate a propensity to cause allergies, rather than prevent them [9,10], and similar findings are reported with propolis [11, 12].

It is also known that some bee products such as bee pollen can induce an allergic reaction in certain individuals, particularly those afflicted by ragweed allergies. The purification of bee products often involves a number of extraction steps to obtain the isolated product. These steps may involve a plurality of organic solvents, saponification and grounding, long periods of time for suspensions to form, separating the bee products from a complex mixture of other botanical compounds and mixing with a number of additives to increase bioactivity.

In addition to the above, a review of the patent prior art confirms that the use of "bee products" has been extensively studied in relation to the various health benefits that may result from the use of such products.

For example, previous work involving bee products include U.S. Pat. No. 7,141,611 by Gamble et al. who extract aliphatic alcohols from beeswax and bee pollen to use as an anti-inflammatory agent in pharmaceuticals, foodstuffs and dietary supplements. U.S. Pat. No. 6,482,442 to Dato discloses a mixture comprising honey and olive oil along with beeswax, propolis, royal jelly, honey and pollen to treat a variety of ailments including inflammation; US Pat. No. 7,351,739 to Ho et al., U.S. Pat. No. 6,342,255 to De Gregorio, 2010/0034905 to Sembrano, U.S. Pat. No. 6,649,178 to Mohammadi et al., and U.S. Pat. No. 6,579,543 to McClung disclose the use of pollen and/or bee pollen to treat inflammation; U.S. Pat. No. 7,763,282 to Corvi Mora et al., and 2010/0074964 to Glavas disclose the use of propolis to treat inflammation; US Patent Publication No. 2005/0048128 to Miyata et al. discloses the use of royal jelly to treat inflammation; and, U.S. Pat. No. 2,494,907 mentions the ability of beeswax bloom to contain applied germ killing sulfa drugs used to prevent the spread of American foulbrood.

While there is increasing commercial interest in natural products to treat inflammation and other related disorders and conditions, there remain problems and issues with existing products which limit their overall usefulness and safety.

It is an object of the present invention to obviate or mitigate some or all of the above noted disadvantages.

SUMMARY OF THE INVENTION

The present invention provides natural anti-inflammatory compositions comprising extracts of wax bloom.

In another aspect, the present invention provides a method of preventing or treating an inflammatory disease in an animal in need of such treatment which comprises administering to said animal a therapeutically effective amount of a composition comprising an extract of wax bloom.

The present invention further provides foods, beverages, nutraceuticals, medicinal formulations, cosmetics, bioceuticals, dietary supplements, health products, condiments and seasonings comprising an extract of wax bloom.

The present invention further provides topical formulations comprising extracts of wax bloom.

In accordance with the invention, there is provided a method of extracting bee bloom from beeswax comprising the step of: solubilizing bee bloom within an aqueous solvent to produce a bee bloom solution.

In another aspect, the invention provides the use of a therapeutically effective amount of bee bloom extract for treatment of inflammation wherein the use may include topical administration.

These and other objects and advantages of the present invention will become more apparent to those skilled in the art upon reviewing the description of the preferred embodiments of the invention, in conjunction with the figures and examples. A person skilled in the art will realize that other embodiments of the invention are possible and that the details of the invention can be modified in a number of respects, all without departing from the inventive concept. Thus, the following drawings, descriptions and examples are to be regarded as illustrative in nature and not limiting.

BRIEF DESCRIPTION OF THE DRAWINGS

Embodiments of the present invention will now be described, by way of example only, with reference to the attached Figures, wherein.

DETAILED DESCRIPTION OF THE INVENTION

A detailed description of one or more embodiments of the invention is provided below along with accompanying figures that illustrate the principles of the invention. As such this detailed description illustrates the invention by way of example and not by way of limitation. The description will clearly enable one skilled in the art to make and use the invention, and describes several embodiments, adaptations, variations and alternatives and uses of the invention, including what we presently believe is the best mode for carrying out the invention. It is to be clearly understood that routine variations and adaptations can be made to the invention as described, and such variations and adaptations squarely fall within the spirit and scope of the invention.

In other words, the invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

In the present disclosure and claims (if any), the word "comprising" and its derivatives including "comprises" and "comprise" include each of the stated integers or elements but does not exclude the inclusion of one or more further integers or elements.

As used herein, the term "about" in connection with a measured quantity, refers to the normal variations in that measured quantity, as expected by a skilled artisan making the measurement and exercising a level of care commensurate with the objective of measurement.

As used herein, the singular forms "a," "an," and "the" include plural referents unless the context clearly dictates otherwise. For example, reference to "a substituent" encompasses a single substituent as well as two or more substituents, and the like.

As used herein, the terms "for example," "for instance," "such as," or "including" are meant to introduce examples that further clarify more general subject matter. Unless otherwise specified, these examples are provided only as an aid for understanding the applications illustrated in the present disclosure, and are not meant to be limiting in any fashion.

As used herein, "animal" means any member of the animal kingdom, including preferably humans.

As used herein, "food" or "food product" or "food material" means any safe, ingestible product for animal use, including human use, and includes "functional foods", dietary supplements, nutraceuticals, and "designer foods".

As used herein "natural health products" refer to vitamins and minerals, herbal remedies, homeopathic medicines, and probiotics As used herein, "functional food" means a product that is similar in appearance to conventional foods that is consumed as part of a usual diet, but which has demonstrated physiological benefits, aside from the pure nutritive advantage.

As used herein, "nutraceutical" means a non-pharmaceutical product prepared in the form of pills, powders, potions and in other medicinal forms not generally associated with food but which has a physiological benefit or provides protection against disease or assists in the treatment of disease or a condition.

As used herein, "bioceutical" refers a healthful compounds or compositions, extracted from natural plants and their derivatives.
Anywhere in the world, nutraceuticals, functional foods, natural health products, bioceuticals, and designer foods may be supplemented with or comprise components which provide medical or health benefits, including the prevention and treatment of disease.

As used herein, topical" means the any topical surface of a subject (e.g., patient), such as skin (including under the scalp), nasal, sinus, vaginal, penile, urinary or anal surfaces.

As used herein, "treatment" means the management and care of a patient for the purpose of combating an inflammatory disease, disorder or condition. The term is intended to include the alleviation, amelioration or relief of symptoms and complications, and/or the cure or elimination of the disease, disorder or condition.

The terms "therapeutically effective amount" or "effective amount" refers to the amount of composition required in order to achieve the desired therapeutic or cosmetic effects.

As used herein, the term "bloom" (also called "fat bloom") refers to the film that forms on the surface of the lipid-based wax composition ("surface fat bloom") or in homogeneities of beta (.beta.) phase crystals that resemble a loosely packed powder within the lipid-based wax composition ("internal fat bloom"). The principle of fat bloom is generally understood to be the transformation of a wax from a metastable phase to a more thermodynamically stable phase. Since fat bloom is a thermodynamically driven process, it will eventually occur in a lipid-based wax composition that is not in its most thermodynamically favoured state, such as a wax composition in the beta prime (.beta.') phase. Although the .beta.' phase is not the most thermodynamically favoured state, the composition of a candle can be designed such that the transformation of the wax from the .beta.' phase to .beta. phase is on the order of years instead of months or days. Fat bloom can also be exacerbated by storage of a candle at an elevated temperature, which can provide the necessary thermal energy for the lipid-based wax composition to undergo phase transformations. Fat crystals on the surface grow in size over time to first produce a dull appearance, with a white or light gray colored deposit on the surface, relative to what was once a glossy surface. Before the white deposit becomes visible, the product usually becomes dull and hazy having lost the high gloss surface. Although texture of the overall product may not be seriously altered by the early stages of fat bloom, the dull appearance and white deposit make it look old and stale to the consumer. Fat bloom may also exhibit itself as growths, which look like cauliflower, forming on the surface or interior of a candle, typically after burning it and then allowing the melt pool to re-solidify.

With respect to beeswax, bloom rises to the surface of a candle when some of the low melting components of the wax migrate to the surface of the candle [13]. It is however, a generally unreported beeswax product. Searches, using the key words "beeswax" and "bloom", in the databases, MEDLINE (OVID), PubMed, Web of Science, and Biological Sciences, did not provide any references to the use of bloom and its composition. The low melting components that compose bloom have not been identified. Beeswax extracted bloom has not experienced the scientific scrutiny observed for other bee products.

Bloom also forms on the cuticular waxes produced by plants and is thought to provide protection against insect parasites, as it reduces attachment surfaces and gives a less adhesive surface [15,16]. Aside from this mechanical function, other actions or effects of beeswax bloom are not known, although the bloom on beecombs appears to have no effects on bees [17], and anti-predator actions have not been discussed.

As noted above, bee bloom is a dusty coating that forms on beeswax over time that is understood to be low melting point components of the beeswax that migrate to the surface of beeswax. In particular, it is commonly seen on aged beeswax candles.

In accordance with the invention, methods of extracting bee bloom, bee bloom compositions and the use of bee bloom are described. In particular, bee bloom is shown to exhibit anti-inflammatory properties as shown by in vitro studies done to study the effect of bee bloom on allergic reactions with intestinal tissues.

Methods of Extraction and Purification

In accordance with the invention, there is provided a method of extracting bee bloom from beeswax comprising the step of: solubilizing bee bloom within an aqueous solvent to produce a bee bloom solution. In another embodiment, step a. includes scraping bee bloom powder from the exterior surfaces of beeswax, suspending the scraped bee bloom powder within the aqueous solvent and removing particulate matter from the aqueous solvent.

Aqueous solvent refers to a substance that acts as a dissolving agent or that is capable of dissolving another substance. The most common solvent is water. Other common solvents which dissolve substances that are insoluble (or nearly insoluble) in water are acetone, alcohol, formic acid, acetic acid, formamide. BTX, carbon disulfide, dimethyl sulfoxide, carbon tetrachloride, chloroform, ether, tetrahydrofuran, furfural, and hexane. They may be classified as polar and non-polar. Polar solvents, like water, have molecules whose electric charges are unequally distributed, leaving one end of each molecule more positive than the other. Usually polar solvent has O—H bond of which water (HOH), (CH$_3$OH) and acetic acid (CH$_3$COOH) are examples. Propanol, butanol, formic acid, formamide are polar solvents. Dipolar solvents which contain a C—O solid bond without O—H bond are acetone [(CH$_3$)$_2$C=O], ethyl acetate (CH$_3$COOCH$_2$CH$_3$), methyl ethyl ketone, acetonitrile, N,N-dimethylformamide and dimethyl sulfoxide. Non-polar solvents, like carbon tetrachloride (CC1$_4$), benzene (C$_6$H$_6$), and diethyl ether (CH$_3$CH$_2$OCH$_2$CH$_3$), have molecules whose electric charges are equally distributed and are not miscible with water. Hexane, tetrahydrofuran and methylene chloride are non-polar solvents. Polar solvents are hydrophilic but non-polar solvents are lipophilic. Polar reactants will dissolve in polar solvents. Non-polar solvents dissolve non-polar compounds best. Oil and water don't mix but separate into two layers. There are three measures of the polarity as "dipole moment", "dielectric constant" and "miscibility with water". Though low dipole moments and small dielectric constants indicates non-polar solvents, sharp boundaries between polar and non-polar solvents are not available. The polarity reflects the balance between a polar component (OH) and a non-polar hydrocarbon component, existing in the same molecule. If hydrocarbon character increases relatively, the polarity decreases. On an operational basis, solvents that are miscible with water are polar.

Preferably, the aqueous solvent comprises one or more hydrophilic components. Alternatively, the aqueous solvent is selected from the group comprising acetone, alcohol, formic acid, acetic acid, formamide. BTX, carbon disulfide, dimethyl sulfoxide, carbon tetrachloride, chloroform, ether, tetrahydrofuran, furfural, and hexane. More preferably, the solvent is aqueous alcohol although other alcohols including, but not limited to methanol and propanol may be used. Most preferably the solvent is aqueous ethanol.

In a more preferred form, the extraction method comprises:
a) Removing bloom from a wax material to form "raw bloom";
b) Drying the raw bloom to form a "dry bloom";
c) Dissolving the dry bloom in an aqueous solvent, as described above.

In a preferred embodiment, the wax material is from beeswax. In a further preferred embodiment, the beeswax or wax material is one or more beeswax candles or was blocks. Drying may occur by evaporation, heating or any other conventional drying step. In a most preferred embodiment, dry bloom is dissolved at step c) in a hydrophilic mixture of alcohol and water (most preferably ethanol and water).

In another embodiment, the concentration of bee bloom in the bee bloom solution is 1.0 mg/ml or greater.

Compositions Extracted from Bloom

In certain preferred embodiments, the compositions of the invention as extracted and purified from wax bloom comprise one or more proteins, fatty acids and peptides.

More preferably, the composition comprises from about 20-30% by weight of the total fatty acids as omega fatty acids, most preferably as omega n-9 fatty acids. Omega n-9 fatty acids (popularly referred to as ω-9 fatty acids) are a family of unsaturated fatty acids which have in common a final carbon-carbon double bond in the n-9 position; that is, the ninth bond from the end of the fatty acid. In a most preferred form, the composition comprises from 20-30% by weight of oleic acid.

Proteins are biochemical compounds consisting of one or more polypeptides typically folded into a globular or fibrous form, facilitating a biological function. A polypeptide is a single linear polymer chain of amino acids bonded together by peptide bonds between the carboxyl and amino groups of adjacent amino acid residues.

The classic assays for protein concentration in food are the Kjeldahl method and the Dumas method and are well known in the art. These tests determine the total nitrogen in a sample. If the amount of nitrogen is multiplied by a factor depending on the kinds of protein expected in the sample, the total protein can be determined. This value is known as the "crude protein" content.

What has surprisingly been found is that the compositions are extracted and purified from wax bloom within the method of the present invention have significantly more crude protein than residual beeswax, and have a significantly higher concentration of long chain fatty acids as compared to beeswax. Even more preferably, the compositions that are extracted and purified from wax bloom have significantly more omega n-9 fatty acids that beeswax, significantly more C16:0 (palmitic acid) than beeswax, significantly more C18:3n3 (alpha linolenic acid) than beeswax, significantly more C24:0 (tetracosanoic acid) than beeswax. Although not intending to be bound by any one theory of action with respect to the anti-inflammatory properties of the composition of the present invention, it is suspected that the noted constituents provide the superior anti-inflammatory action in combination and at the elevated levels as compared to beeswax extracts.

In one preferred form, the composition is a bee bloom extract comprising a ratio of C16:0 to C18:1 n9 of from about 1.4 to 1.6:1. In one preferred form, the composition is a bee bloom extract comprising a ratio of C18:1n9 to C18:3n3 of from about 5 to 7:1. In one preferred form, the composition is a bee bloom extract comprising a ratio of C16:0 to total crude protein of about from about 2.2 to 2.9:1.

In a most preferred embodiment, the extract composition comprises the entire middle column of enumerated constituents in Table 1.

Uses of Compositions

It is contemplated that the composition of the present invention may be beneficially applied to animals in topical formulations to treat or ameliorate an inflammatory condition. For external application, the composition may be formed into creams, ointments, gels, sprays, lotions, skin tonics, shampoos or mousses. Skin sprays are generally composed of aerosolized copolymers, such as polyvinylpyrrolidone, vinyl acetate and the like, and may also function as a setting lotion. Skin gel preparations are similar to sprays in composition, but are in gel and alcohol free form, and can coat the skin. Skin mousse is foam released under pressure from an aerosolized can. A skin care composition may be formulated as a hydrophobic or hydrophilic cream, ointment, gel, emollient, spray, lotion, skin tonic, shampoo or mousse, suitably with additional (optional) ingredients suitable for use in skin care compositions of types known in the art, and such further ingredients can include petrolatum, waxes, lanolin, silicone, liposomes, vegetable, mineral oils, plasticizers, fragrances, preservatives, a penetration enhancing agent, a pH adjusting agent or other suitable ingredients for topical skin compositions. Such ingredients can moisturize skin, stabilize the active compound, increase drug-skin contact and local concentration, control drug slow release, and/or aid in decreasing skin breakage, preventing skin atrophy, fibrosis and infection, and promoting skin wound healing, if desired.

The present invention further provides a method of treating or ameliorating an indication of non-mucosal topical tissue comprising periodically applying to such disease or condition affected tissue a composition comprising an effective amount of an appropriate composition of the wax bloom extract.

The invention further comprises applying the composition onto or within a portion of a film, patch or an adhesive solid formulation. The invention also provides lotions, gels, creams, ointments or suppositories comprising: an effective amount of appropriate composition of herbal bioactive comprising active(s) as described herein, optionally wherein the composition further forms a mucoadhesive coating on mucosal surfaces.

The compositions of the invention can be formulated in any of the many compositions used in topical or mucosal treatments. For example, the compositions can be formulated as baths or soaks, solutions, lotions, gels, creams, ointments, suppositories, dressings adapted to release the compositions, instillation solutions, foams, or the like. In certain embodiments, the compositions are applied in reservoir or adhesive patches, or in films (such as described in US2007/149902).

In certain embodiments, the combination is formulated in a lotion, gel, cream, ointment or suppository.

Other Dosage Forms

The present invention provides a method for treating or preventing inflammation including coronary plaque inflammation, bacterial-induced inflammation, viral induced inflammation and inflammation associated with wounds, acute pain and surgical procedures which comprises administering to an animal, a non-toxic and therapeutically effective amount of a composition comprising extracted and purified wax bloom.

It has surprisingly been found that the extracts and compositions of the present invention exhibit superior anti-inflammatory activity and as such have a wide variety of therapeutic and cosmetic applications.

In certain embodiments, the composition is administered in conjunction with another administration form, such as a film, patch or mucoadhesive solid dosage form. This solid dosage form can be applied before, concurrently, or after administration of the composition. The solid forms can help deliver medicament to more severely affected, or more mechanically accessible tissue, while the composition delivers medicament elsewhere. The medicament in the solid form can be the same or different from that of the compositions of the invention. For example, the dosage forms described in WO 02/094300 and U.S. Pat. No. 7,285,295 can be employed. Or, the film described in the an application, filed Jun. 20, 2007, titled "Anti-Inflammatory Dissolvable Film", Ser. No. 11/765,587, can be employed.

In certain embodiments, the other dosage form is adapted for systemic administration, such as by oral dosage form or by i.v.

The desired effects described herein may be achieved in a number of different ways. The compounds and compositions of the present invention may be administered by any conventional means available for use in conjunction with pharmaceuticals, nutraceuticals, foods, beverages, and the like.

A pharmaceutical composition for treating inflammation including coronary plaque inflammation, bacterial-induced inflammation, viral induced inflammation and inflammation associated with wound, acute pain and surgical procedures said composition comprises a wax bloom extract as described herein and an optional adjuvant or carrier.

A method for treating and reducing inflammation including coronary plaque inflammation, bacterial-induced inflammation, viral induced inflammation and inflammation associated with wounds, acute pain and surgical procedures which comprises administering to an animal, a non-toxic and therapeutically effective amount a wax bloom extracts as described herein and an optional adjuvant or carrier.

Dosages—

The amount of the compound or composition which is required to achieve the desired therapeutic or cosmetic effects will, of course, depend on a number of factors such as the mode of administration and the condition and size of the animal (subject to be treated). Such dose adaptation is well within the purview of someone skilled in the art.

However, as a guideline, assuming a molecular weight of about 300 Daltons for the active ingredients in the bloom extract, an effective clinical dose of the composition, when administered orally may be as follows, based on per kg weight of subject:

From about 100µg/kg to 3 mg/kg
More preferably from about 100µg/kg to µ1 mg/kg
More preferably from about 500 µg/kg to 800µg/kg narrow range Lower doses than those ascribed above may be sufficient for topical applications, and could possibly be about 10 µg to 1 mg per dose (or even lower); i.e. at least 70 times less than needed with oral ingestion.

The compounds and compositions of the present invention can be administered to a patient either by:
Topical application
Within pharmaceutical compositions where they are mixed with suitable carriers or excipients for oral, buccal, or other conventional use.
Mixed within foods
Mixed within beverages
Mixed within nutraceuticals
Mixed within dietary supplements such as vitamins and chewables
Combined as part of bioceutical formulation Use of physiologically acceptable carriers to formulate the compounds and compositions herein disclosed for the practice of the invention into dosages suitable for systemic administration is within the scope of the invention. With proper choice of carrier and suitable manufacturing practice, the compounds and compositions of the present invention, in particular, those formulated as solutions, may be administered parenterally, such as by intravenous injection. The compounds and compositions can be formulated readily using pharmaceutically acceptable carriers well known in the art into dosages suitable for oral administration. Such carriers enable the compounds and compositions of the invention to be formulated as tablets, pills, capsules (including soft gel capsules), liquids, gels, syrups, slurries, suspensions and the like, for oral ingestion by a patient to be treated.

Pharmaceutical compositions, comprising one or more of the compounds of the present invention, include compositions wherein the active ingredients are contained in an effective amount to achieve their intended purpose. Determination of the effective amounts is well within the capability of those skilled in the art, especially in light of the detailed disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The delivery compositions of the present invention may be manufactured in a manner that is itself known, e.g., by means of conventional mixing, dissolving, granulating, dragee-making, levigating, emulsifying, encapsulating, entrapping or lyophilizing processes.

Formulations for parenteral administration include aqueous solutions of the bloom extraction composition in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Preparations for oral use can be obtained by combining the active compositions with solid excipient, optionally grinding a resulting mixture, and processing the mixture of granules, after adding suitable auxiliaries, if desired, to obtain tablets or dragee cores. Suitable excipients include lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

In another form of the present invention, the compounds and compositions of the present invention may be administered through foods, beverages and nutraceuticals, including, without limitation, the following:

1) Dairy Products—such as cheeses, butter, milk and other dairy beverages, spreads and dairy mixes, ice cream and yoghurt;
2) Fat-Based Products—such as margarines, spreads, mayonnaise, shortenings, cooking and frying oils and dressings;
3) Cereal-Based Products—comprising grains (for example, bread and pastas) whether these goods are cooked, baked or otherwise processed;
4) Confectioneries—such as chocolate, candies, chewing gum, desserts, non-dairy toppings (for example Cool Whip®), sorbets, icings and other fillings;
5) Beverages—whether alcoholic or non-alcoholic and including colas and other soft drinks, juice drinks, dietary supplement and meal replacement drinks such as those sold under the trade-marks Boost® and Ensure®; and
6) Miscellaneous Products—including eggs and egg products, processed foods such as soups, pre-prepared pasta sauces, pre-formed meals and the like.

The compounds and compositions of the present invention may be incorporated directly and without further modification into the food, nutraceutical or beverage by techniques such as mixing, infusion, injection, blending, dispersing, emulsifying, immersion, spraying and kneading. Alternatively, the compounds and compositions may be applied directly onto a food or into a beverage by the consumer prior to ingestion. These are simple and economical modes of delivery.

While the forms of composition, method and process described herein constitute preferred embodiments of this invention, it is to be understood that the invention is not limited to these precise forms. As will be apparent to those skilled in the art, the various embodiments described above can be combined to provide further embodiments. Aspects of the present composition, method and process (including specific components thereof) can be modified, if necessary, to best employ the systems, methods, nodes and components and concepts of the invention. These aspects are considered fully within the scope of the invention as claimed. For example, the various methods described above may omit some acts, include other acts, and/or execute acts in a different order than set out in the illustrated embodiments.

Further, in the methods taught herein, the various acts may be performed in a different order than that illustrated and described. Additionally, the methods can omit some acts, and/or employ additional acts.

These and other changes can be made to the present systems, methods and articles in light of the above description. In general, in the following claims, the terms used should not be construed to limit the invention to the specific embodiments disclosed in the specification and the claims, but should be construed to include all possible embodiments along with the full scope of equivalents to which such claims are entitled. Accordingly, the invention is not limited by the disclosure, but instead its scope is to be determined entirely by the following claims.

EXAMPLES

Example 1

Extraction and Purification Steps

Materials and Methods

Bee bloom was obtained by scraping beeswax candles with a scalpel. The wax candles were acquired through a local retailer and were all obtained from the same batch. The beeswax candles were roughly 1-2 weeks old prior to use. The wax in the beeswax candles were from a chemical free farm. No vitamin E, nut oil or animal by products were included in the wax.

The candles were stored in sealed glass jars at an ambient temperature of 15° C. for several weeks, which was sufficient time for bloom to appear on the surface of the candle, The candles were scraped and the scrapings were collected into a glass container sealed with a metal lid and stored at 15° C. The product obtained from scraping the candles contained beeswax contaminants which were removed by extraction with alcohol. The Bee Bloom could also be isolated from beeswax by washing it with a water/ethanol mixture with or without mechanical effects such as agitation and/or sonication.

Bee Bloom was extracted from the beeswax scrapings into a 1 ml mixture of 70% ethanol and 30% filtered water. The solution was sonicated 5 times for 1 minute and the resulting suspension centrifuged at 500 rpm (approx. 40 grams of force) for 3 minutes to remove large particulate matter. The particulate matter was primarily beeswax. The supernatant was collected and stored in 500 ml aliquots at −20° C. A reference stock solution contained 10 mg/ml Bee Bloom and the dilutions used in the study were in nanograms (ng/ml; $10^9$ g/ml). All dilutions from the stock solution (supernatant) were made in Krebs buffer. Sample sizes used for the study are shown in Table 1.

TABLE 1

N-values for different doses of Bee Bloom added to millilitre of organ bath volume.

| Nanograms/ml | N |
|---|---|
| 100.0 | 7 |
| 35.0 | 5 |
| 10.0 | 7 |
| 3.5 | 5 |
| 1.0 | 7 |

Example 2

In Vivo Rat Study

Statistical Analysis

Data are expressed as the mean +/− standard error. The data were analyzed using Student's t test for paired samples. Significant differences were accepted if p <0.05. Outlier analysis was performed using a modified Z-score that uses the median of absolute deviation A Z-score with an absolute value of greater than 4.0 was labeled as a potential outlier, and the corresponding data value was excluded.

Animals

Male Sprague Dawley rats (Charles River Laboratories, Montreal, QC) of initial weights of 150 g were maintained with lights on from 700 to 1900 h and given food and water ad libitum. The rats were sensitized to 1 mg ovalbumin (OA) using 50 ng of pertussis toxin (Sigma-Aldrich, St. Louis, Mo.) as an adjuvant.

In Vitro Anaphylaxis

Five to eight weeks following sensitization, the terminal duodenum of the rats was excised and 1 cm sections were mounted in 25 ml organ baths, containing bicarbonate Krebs' buffer, with 1.0 g of tension. The isometric force generated in response to OA and carbachol (CAR; (2-[(aminocaronyl) oxy-N,N,N-trimethylethanaminium), a cholinergic agonist, (Sigma-Aldrich) was measured using a Grass Force Displacement Transducer FTO3 (Quincy, MA>. Data were recorded with PolyView software (Polybytes, Inc., Cedar Rapids, Iowa). The tissues were allowed to equilibrate for 30 min during which they were washed several times with buffer, and applied tension was adjusted.

Eight tissue segments were mounted in separate tissue baths, with one tissue segment serving to evaluate if the intestinal tissues elicit a contractile response to the antigen. The other tissues were treated with one of the concentrations of Bee Bloom. A minimum of 4 intestinal segments from 4 different animals wore used for each dose of Bee Bloom. In the absence of a contractile response to antigen the tissues were discarded, and another animal taken.

A control anti-allergic compound (the peptide D-phenylalanine-D-glutamate-Glycine (feG)) was used at a dose of $10^{-8}$ M. This compound is a Control in the Figures.

Anti-anaphylactic properties of the Bee Bloom were determined by adding Bee Bloom to separate baths and incubating for 10 min, before challenging with 1 mg of the AR antigen. Once peak contractile responses were attained the tissues were washed three times, baseline re-established and peak contractile response to $10^{-5}$M CAR obtained. The mucosa was then scraped from the tissue, and the mass of the muscle determined. Responses were determined as grams of force/mg wet tissue.

Contractile responses to OA and CAR were measured at peak contraction, and calculated as grams of force per gram wet tissue. Results are expressed in three formats:
  i) the amplitude of the OA-induced contractile response (grams of force/mg wet tissue),
  ii) the ratio of the Bee Bloom response to the OR response (Bee Bloom/OA) (i.e. animal matched control),
  iii) the ratio of the OA and CAR-induced contractile responses (ONCAR) (i.e. tissue matched controls).

Example 2A

Effect of Bee Bloom on Allergic Reactions with Intestinal Tissues

OA-Induced Contractile Response

Figure 1:
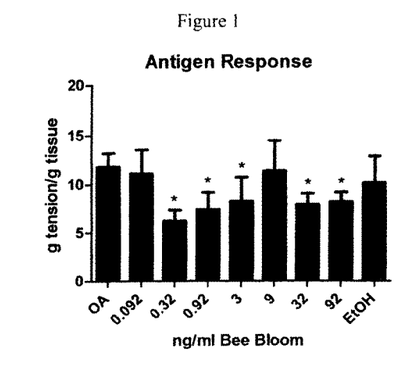
FIG. 1 is a plot of the results from an in vitro study showing the effect of Bee Bloom on the ovalbumin induced contractile response of sensitized rat intestine.
Figure 2:
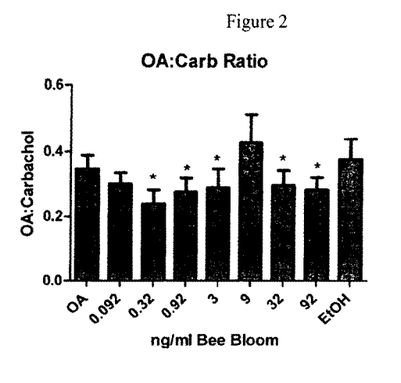
FIG. 2 is a plot of the results from an in vitro study showing the effect of Bee Bloom on the ovalbumin-induced contractile response of sensitized rat intestine when normalized to the response of an antigen alone.

Two doses of Bee Bloom (3.5 and 35 ng/ml) significantly inhibited antigen-elicited contractions of the sensitized rat intestine when data are presented in g tension/g tissue (FIG. 1). When normalized to the antigen (OR) response, three doses (3.5, 10 and 35 ng/ml) of Bee Bloom exhibited a significant inhibition of the antigen-induced contractions (FIG. 2). These differences reflect an abnormally higher response (outlier) at the 10 ng/ml dose of Bee Bloom. The control significantly inhibited the antigen-induced contractions.

Ratio of the Bee Bloom Response to the OA Response

Figure 3:
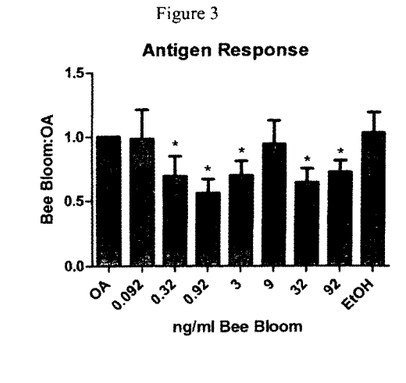
FIG. 3 is a plot of the results from an in vitro study showing the effect of Bee Bloom as the ratio of Bee Bloom contractile response to the ovalbumin-induced contractile response of sensitized rat intestine; and, FIG. 4 is a plot of the results from an in vitro study showing the effect of Bee Bloom as the ratio of Bee Bloom contractile response with antigen to Bee Bloom contractile response with carbachol in sensitized rat intestine.

When the ratio of the contractile responses of Bee Bloom and CA was considered (i.e. animal matched control), Bee Bloom gave significant inhibition of the antigen-induced contractions of the sensitized rat intestine at 3.5, 10 and 35 ng/ml (FIG. 3). The control significantly inhibited the antigen-induced contractions.

Ratio of the OA and CAR-Induced Contractile Responses

Figure 4:
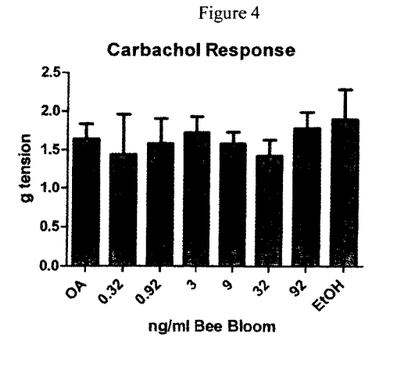

With the OA:CAR ratios (i.e. tissue matched controls) Bee Bloom gave significant inhibition of the antigen-induced contractions of the sensitized rat intestine at 35, 10 and 35 ng/ml (FIG. 4). The control did not significantly inhibit the OA:CAR ratio.

Discussion

Bee Bloom at doses of 3.5, 10 and 35 ng/ml significantly inhibited antigen-induced contractions of the sensitized rat intestine. This inhibition was observed for raw data (FIGS. 1 and 2), animal-matched controls (FIG. 3), and tissue-matched controls (FIG. 4). The −40% inhibition seen with Bee Bloom matches closely that seen with the control.

The method used to extract Bee Bloom would favour the collection of lipid molecules, although some hydrophilic proteins would also be extracted. Although bee pollen is the precursor for all bee products (propolis, royal jelly, honey, beeswax, bee bread and Bee Bloom), bee pollen and Bee Bloom have distinct compositions since Bee Bloom was dissolved in a relatively hydrophilic mixture of water and ethanol, whereas solvents with low hydrophilicity, such as dichloromethane, or chloroform:methanol mixtures, are used to extract bees wax. Water:ethanol extraction would tend to isolate the free fatty acids, free primary fatty alcohols and proteins rather than the wax esters and straight hydrocarbons.

Bee bloom in accordance with the invention may be effective in the treatment of inflammation in a variety of forms including incorporation into topical skin creams, lozenges, and capsules.

Although the present invention has been described and illustrated with respect to preferred embodiments and preferred uses thereof, it is not to be so limited since modifications and changes can be made therein which are within the full, intended scope of the invention as understood by those skilled in the art.

Example 3

Bloom Extract Analysis

POS was contracted to extract and analyze the composition of bloom from beeswax. In addition, the storage conditions for bloom development were evaluated.

Objectives

1 Evaluation of storage conditions suitable for bloom development.
2. Extraction of bloom from beeswax using the method provided by the client.
3. Compositional analyses (including total phenolic content, residual solvents, fatty acid composition, total fatty alcohol content, crude protein content and elemental analysis) of bee bloom and residual beeswax.

1. Materials and Methods 1.1 Materials

Beeswax (blocks and candles) were used for the processing trials.

Anhydrous ethanol used for the bloom extraction was purchased from Commercial Alcohols, Winnipeg, MB.

1.2 Equipment

Vacuum oven: Fisher ISOTEMP vacuum oven model 281 (Fisher Scientific, Toronto, ON).

Rotary Vacuum Evaporator: Buchi Rotavapor R-151 rotary vacuum evaporator (Brinkmann Instruments, Mississauga, ON).

Processing Methods

Bloom Development

To increase surface area for bloom development on the Beeswax blocks and candles, some blocks were liquefied and poured into shallow rectangular dishes to form beeswax sheets. Beeswax sheets and blocks were stored at room temperature both in the dark as well as under the light. As per client request, one sample of wax sheet was kept in a glass vacuum jar at room temperature. In addition, three candles were burned for 4 hours, and then stored in the dark to aid bloom development (24).

Bloom Extraction

Beeswax candles, blocks and sheets were scrapped with a metal spatula. Bloom was extracted according to the method provided in example 1. After extraction, both bloom and residual beeswax was dried in a rotatory evaporator and vacuum oven to obtain the total dry weight. Dried bloom was then dissolved in 100 ml 70% ethanol and held in a refrigerator prior to compositional analyses.

Compositional Analyses

The vacuum oven dried bloom extract and residual beeswax were subjected to the following analyses:

Crude protein: AOCS Ba 4e-93
Total fatty acid composition: AOAC 969.33
Total phenolic content: modified method of Slinkard and Singleton method (29) Total fatty alcohol: modified method of Jimenez et al (25))

In addition, residual beeswax was subjected to the following analyses:

Elemental analysis: AOCS Ca20-99
Residual solvent: AOCS Cg 4-94

Results and Discussion

Bloom Development

Bloom Extraction

A total of 0.59 g dried bloom was extracted and dissolved in 100 ml 70% ethanol. The bloom/ethanol stock solution (5.9 g/ml), which was light yellow in color, were stored in a refrigerator and used for compositional analyses. A white fluffy precipitate was observed when the solution was stored in refrigerator.

Compositional Analysis

Total phenolic content, crude protein, total fatty acids and total fatty alcohols content of both the bloom and residual beeswax are shown in Table 2. The crude protein content, which was estimated based on the total nitrogen present in the sample, was significantly higher in the bloom extract compared to that of the residual beeswax. According to the literature (25), hydroxy fatty acids were observed in beeswax, however, due to the difference of GC column, hydroxy fatty acid was not identified in the present analysis. No fatty alcohol was detected in the bloom extract whereas four saturated fatty alcohols were identified in the residual beeswax.

Some studies have suggested that the anti-allergic effect of bee pollen, which contains about 35% protein, may be attributed to the presence of phenolic compounds, higher aliphatic primary alcohols and lipid-soluble components in pollen (26, 27 and 28). In the current study, phenolic content and aliphatic alcohols in residual beeswax were significantly higher than those in bloom extract. However, nitrogen-containing compounds (such as protein, peptides, amino acids), $C16:0$, $C18:1n9$ and $C18:3n3$ were significantly higher in the bloom composition of the present invention.

TABLE 2

Compositional analysis of bloom extract and residual beeswax.

| Analyses (expressed as mg/g sample) | Bloom extract | Residual beeswax |
|---|---|---|
| Total phenolic content[1] | 3.2 | 248 |
| Crude protein | 40.8 | 3.4 |
| Total fatty acid composition[2] | | |
| $C12:0$ | 1.3 | 0.3 |
| $C14:0$ | 1.9 | 0.4 |

TABLE 2-continued

Compositional analysis of bloom extract and residual beeswax.

| Analyses (expressed as mg/g sample) | Bloom extract | Residual beeswax |
|---|---|---|
| C15:0 | 0.2 | ND |
| C16:0 | 115.8 | 60.1 |
| C16:1n7 | 2.0 | 0.2 |
| C17:0 | 0.3 | ND |
| C17:1 | 0.4 | 0.1 |
| C18:0 | 7.3 | 2.6 |
| C18:1n9 | 71.8 | 10.7 |
| C18:1 | 0.7 | 0.1 |
| C18:2 | 7.7 | 0.2 |
| C18:3n3 | 11.8 | 6.1 |
| C18:4 | ND | 0.2 |
| C20:0 | 1.3 | 1.0 |
| C20:1 | 2.2 | 0.6 |
| C20:5n3 | ND | 0.2 |
| C22:0 | 8.4 | 2.7 |
| C22:1n9 | 0.8 | 0.1 |
| C21:5n3 | ND | 0.1 |
| C22:4n6 | 0.3 | 14.7 |
| C22:5n6 | 0.4 | 0.2 |
| C24:0 | 21.3 | 27.4 |
| C24:1n9 | 1.7 | ND |
| Others | 10.1 | 4.6 |
| Total fatty acids | 267.7 | 132.6 |
| Total Saturates | 157.8 | 94.5 |
| Total monounsaturates | 79.6 | 11.8 |
| Total polyunsaturates | 20.2 | 21.7 |
| Total omega 3 | 11.8 | 6.6 |
| Total omega 6 | 8.4 | 13.1 |
| Total omega 9 | 76.5 | 11.4 |
| Total fatty alcohol[3] | | |
| C24:0 | ND | 0.69 |
| C26:0 | ND | 0.62 |
| C28:0 | ND | 0.74 |
| C30:0 | ND | 1.7 |

[1]Total phenolic content is expressed as mg gallic acid equivalent per g sample.
[2]Only common fatty acids are listed here. Unusual fatty acids, such as hydroxy fatty acids and branched chain fatty acids, were not analyzed.
[3]Saturated fatty alcohols up to 30 carbon chain length were identified.
ND: not detected.

Residual solvent and elemental analysis of residual beeswax were shown in Table 3. Due to the limited amount of bloom extract sample, residual solvent and presence of elements were not measured.

TABLE 3

Residual solvent (ethanol) and elemental analysis of residual beeswax.

| Analyses | Residual beeswax |
|---|---|
| Residual solvent | Ethanol <1.0 ppm |
| Elemental analysis | |
| Phosphorus | 5.60 ppm |
| Magnesium | 0.94 ppm |
| Potassium | <0.50 ppm |
| Sodium | <0.50 ppm |
| Calcium | 9.26 ppm |
| Copper | <0.05 ppm |
| Iron | 1.38 ppm |

REFERENCES

1. Fields D. The Health Benefits of Bee Products. 2010 [cited 2010 Oct. 25, 2010]; Available from: http://www.suite101.com/content/the-benefits-of-bee-products-a292871.
2. Lyngheim L, Scagnetti J. Bee Pollen: Nature's Miracle Health Food, Hollywood, Calif.: Wilshire Book Company, 1979.
3. Hellner M, Winter D, von Georgi R, Munstedt K. Apitherapy: usage and experience in german beekeepers. Evid Based complement Alternat Mod 2008; 5(4):475-479.
4. Campos M, Markham K R, Mitchell K A, Proenca da Cunha A. An Approach to the Characterization of Bee Pollens via their Flavonoid/Phenolic Profiles. PHYTOCHEMICAL ANALYSIS 1 997; 8:1 81-185.
5. Stickl H, Kerscher G. (Treatment of hay fever with new pollen capsules]. Fortschr Med I 980; 98(1 0):343-346.
6. Ishikawa Y, Tokura T, Ushlo H, Niyonsaba F, Yamamoto '1, Tadokoro T, et al. Lipid-soluble components of honeybee-collected pollen exert antiallergic effect by Inhibiting IgE-mediated mast cell activation in vivo. Phytother Res 2009; 23(10:1581-1586.
7. Mendoza S, Noa M, Perez Y, Mas R. Preventive effect of D-002, a mixture of long-chain alcohols from beeswax, on the liver damage induced with CCl4 in rats. J Med Food 2007; 1 O(2):379-383.
8. Mas R. D-002. Drugs of the Future 2001; 26:731-744.
9. Garcia M, del Pozo M D, Diez J, Munoz 0, de Corres L F. Allergic contact dermatitis from a beeswax nipple-protective. Contact Dermatitis 1 995; 33(6):440-441.
10. Harper J I, Gray W, Wilson-Jones E. Cryoglobulinaemia and angiomatosis. Br J Dermatol 1 983; 1 09(4):453-458.
11. Jensen C D, Andersen K E. Allergic contact dermatitis from cera alba (purified propolis) in a lip balm and candy. Contact Dermatitis 2006; 55(5):31 2-313.
12. Rajpara S, Wilkinson M S, Kng C M, Gawkrodger D J, English J S, Statham B N, et al. The importance of propolis in patch testing—a multicentre survey. Contact Dermatitis 2009; 61 (5): 287-290.
13. Van Allen J. Annie's Apitherapy. 2010 [cited 2010; Available from: http://www.anniesapitherapy.com/beeswax.htm.
14. Small A V, Small AVSmall AVs; Beecomb Foundation, assignee. Title Unknown. U.S. Pat. No. 2,494,907. 1947.
15. Duotting P S, Ding H, Neuteld J, Eigenbrode S D. Plant waxy bloom on peas affects infection of pea aphids by Pandora necaphidis. J lnvertebr Pathol2003; 84(3):149-158.
16. Eigenbrode S D. The effects of plant epicuticular waxy blooms on attachment and effectiveness of predatory insects. Arthropod Struct 0ev 2004; 33(1):91-102.
17. Lyttle S. Lyttle P. New Zealand Beeswax Ltd. 2010 Oct. 10, 2010 [cited 2010 Oct. 25, 2010]; Welcome to New Zealand Beeswax Ltd. http://www.beeswax.co.nZ/iflfOrmatiOrLhtm.
18. Metwally E, Pires J M, Moore G J, Bet us D A, Davison J S, Mathison ft Submandibular gland tripeptide FEG (Phe-Glu-Gly) and analogues: keys to structure determination. Peptides 200223(1):1 93-199.
19. Kosecka U, Marshall J S, Crowe S E, Bienenstock J, Perdue MI-I. Pertussis toxin stimulates hypersensitivity and enhances nerve-mediated antigen uptake in rat intestine. Am J Physic! 1994; 267(5 Pt 1):G745-753.
20. Iglewicz B, Hoaglin D. Volume 16: How to Detect and Handle Outliers, 1993.
21. Methods NSe-HoS. Detection of Outliers—page—1.3.5.17. 2010 [cited 2010 Jul. 30, 2010]; Available from: httpl/www.itl.nist.gov/div898/handbook/
22. lshikawa Y, Tokura T, Nakano N, Hara M, Niyonsaba F, Ushio H, et al, inhibitory effect of honeybee-collected pollen on mast cell degranulation in vivo and in vitro. J Med Food 2008; 11(1):14-20.
23. Medeiros K C P, Figueiredo C A V, Figueredo T B, Freire K R L, Santos F A R, Alcantara Neves N M, et al. Anti-allergic effect of bee pollen phenolic extract and myricetin in ovalbumin-sensitized mice. Journal of Ethnopharmacalogy 2008; 1 19:41-46.
24. How to Create Bloom on Beeswax Candles.http://www.ehow.com/how_4866142_create-bloom-beeswax-candles.html—retrieved Nov. 8, 2011.
25. Jiminez, J. J., Bernal, J. L., Aumente, S., Toribio, J. B. Jr. (2003) Quality assurance of commercial beeswax 11. Gas chromatography-electron impact ionization mass spectrometry of alcohols and acids. Vol. 1007, 101-116.
26. Medeiros, K. C., Figueiredo, C. A., Figueredo, T. B., Freire, K. R., Santos, F. A, Alcantara-Neves, N. M., Silva, T. M., Piuvezam, M. R. (2008) Anti-allergic effect of bee pollen phenolic extract and myricetin in ovalbumin-sensitized mice. Vo 1.119, 41-46.
27. Mendoza, S., Noa, M., Pbez, Y., Mas, R. (2007) Preventive effect of D-002, a nixture of long-chain alcohols from beeswax, on the liver damage induced with CCl4 in rats. Vol. 10, 379-383.
28. Ishikawa, Y., Tohura, T., Niyonsaba, F., Yamamoto, Y., Tadokoso, T., Ogawa, H., Okumura, K. (2009) Lipid-soluble components of honeybee-collected pollen exert allergenic effect by inhibiting IgE-mediated mast cell activation in vivo. Vol. 23, 1581-1586.
29. Slinkard, K. & Singleton, V. L. (1977) Total Phenol Analysis: Automation and Comparison with Manual Methods. Am. J. Enol. Vitric, Vol. 28 (1). 49-55

The invention claimed is:

1. A topical anti-inflammatory composition comprising an effective amount of a beeswax bloom extract,
wherein said extract is obtained by extracting beeswax bloom powder with aqueous ethanol,
wherein the extract comprises at least one crude protein, at least one long chain fatty acid, and at least one peptide,
wherein the extract comprises at least 1.5 times more $C16:0$ fatty acids than in beeswax expressed as mg/g, and at least 10 times more crude protein than in beeswax expressed as mg/g, and
wherein said composition is formulated as a topical cream, ointment, gel, spray, lotion, shampoo or mousse.

2. The composition of claim 1 wherein from about 20-30% by weight of total fatty acids in the extract are omega n-9 fatty acids.

3. The composition of claim 1 comprising a ratio of $C16:0$ to $C18:1n9$ fatty acids of from about 1.4 to 1.6:1.

4. The composition of claim 1 comprising a ratio of $C18:1n9$ to $C18:3n3$ fatty acids of from about 5 to 7:1.

5. The composition of claim 1 comprising a ratio of $C16:0$ fatty acids to total crude protein of about from about 2.2 to 2.9:1.

6. A method of treating an inflammatory disease in a subject in need thereof comprising topically administering an effective amount of the composition of claim 1 to said subject.

7. A method of producing a beeswax bloom extract comprising:
(a) obtaining a beeswax bloom powder;
(b) suspending the beeswax bloom powder in aqueous ethanol to obtain a beeswax bloom solution; and
(c) removing particulate matter from the beeswax bloom solution to obtain said extract,
wherein the extract comprises at least one crude protein, at least one long chain fatty acid, and at least one peptide, and
wherein the extract comprises at least 1.5 times more $C16:0$ fatty acids than in beeswax expressed as mg/g, and at least 10 times more crude protein than in beeswax expressed as mg/g.

* * * * *